United States Patent [19]

Scibetta

[11] Patent Number: 4,573,474

[45] Date of Patent: Mar. 4, 1986

[54] CABLE HARNESS FOR AN ELECTROCARDIOGRAM DEVICE

[76] Inventor: James S. Scibetta, 255 Hosea Ave., #1, Cincinnati, Ohio 45220

[21] Appl. No.: 635,254

[22] Filed: Jul. 27, 1984

[51] Int. Cl.$^4$ .............................................. A61B 5/04
[52] U.S. Cl. .................................... 128/644; 128/639; 128/696; 128/802
[58] Field of Search .................. 128/419 D, 639, 644, 128/695–696, 731, 802

[56] References Cited

U.S. PATENT DOCUMENTS

| | | | |
|---|---|---|---|
| 2,249,935 | 7/1941 | Birtcher | 128/413 |
| 3,055,372 | 9/1962 | Browner | 128/421 |
| 3,196,877 | 7/1965 | Corbin | 126/406 |
| 3,411,495 | 11/1968 | Casby | 128/644 |
| 3,703,900 | 11/1972 | Holznagel | 128/419 D |
| 3,792,700 | 2/1974 | Sarnoff et al. | 128/2.06 |
| 3,888,240 | 6/1975 | Reinhold, Jr. et al. | 128/696 |
| 3,910,260 | 10/1975 | Sarnoff et al. | 128/2.06 |
| 3,991,747 | 11/1976 | Stanly et al. | 128/2.06 |
| 4,033,333 | 7/1977 | DeSalvo et al. | 128/2.06 |
| 4,233,987 | 11/1980 | Feingold | 128/639 |
| 4,308,870 | 1/1982 | Arkans | 128/640 |
| 4,328,814 | 5/1982 | Arkans | 128/640 |
| 4,353,372 | 10/1982 | Ayer | 128/640 |
| 4,354,509 | 10/1982 | Strahwald et al. | 128/639 |
| 4,457,309 | 7/1984 | Elmeskog | 128/644 |

FOREIGN PATENT DOCUMENTS

| | | | |
|---|---|---|---|
| 576083 | 5/1933 | Fed. Rep. of Germany | 128/802 |
| 930855 | 2/1948 | France | 128/802 |

Primary Examiner—William E. Kamm
Assistant Examiner—Mitchell J. Shein
Attorney, Agent, or Firm—Frost & Jacobs

[57] ABSTRACT

A cable harness device for use with an EKG machine in which the cable harness device includes a central unit having spring biased laterally extending arms, side arms perpendicularly attached to the lateral arms, a swivel joint mounted on top of the central unit, a boom attached to the swivel joint; and a plurality of EKG electrodes attached to the boom, lateral arms, and side arms to monitor the electrical activity of the heart. The cable harness device of the present invention permits the operator to quickly remove the chest electrodes attached to the boom by rotating the boom away from the chest in order to permit heart message if cardiac arrest occurs while the patient is attached to the EKG machine. This arrangement also permits the side arm and lateral electrodes to remain attached to the patient to monitor the electrical activity of the heart while heart message is being given. In the event that it may be necessary to quickly remove the entire cable harness device, the apparatus can be grasped at the central unit and merely pulled upwardly and away from the patient which will detach all the electrodes from the patient. Furthermore, the device of the present invention is adapted to be employed on a wide variety of sizes of patients since the lateral arms are spring biased since the side arm and lateral arm electrodes are telescopically adjustable.

21 Claims, 8 Drawing Figures

CABLE HARNESS FOR AN ELECTROCARDIOGRAM DEVICE

BACKGROUND OF THE INVENTION

1. Field Of The Invention

The present invention concerns an electrocardiogram sometimes referred to as EKG or less often referred to as ECG. In particular, the present invention relates to a cable harness containing the leads which are positioned on various points of the patient's body and extend from the patient's body to the EKG machine.

2. Description Of The Prior Art

Generally electrocardiograms, generally referred to as EKG have ten cable leads which attach to various points on the upper and mid-torso of a patient to measure and analyze cardiac data. One of the most common frustrating problems associated with the operation of an EKG concerns the degree of difficulty in setting up and operating the EKG. In particular, the technician or nurse in charge of coupling the EKG to a patient often becomes entangled with the ten cable leads of the EKG. Moreover, because the lines may tangle with one another, a frequent problem exists wherein the leads detach from the patient and drop to the floor before or during the operation of the EKG device. When this happens, the nurse or technician must stop and reattach the lead to the patient at its rightful location. As a result of the above problems, the time required to set up and operate the device becomes very lengthy.

Another problem associated with the installation of the EKG device centers around the fact that the EKG device is employed to monitor the electrical activity of the heart, particularly after the patient has had a heart attack, in order to determine the damage to the heart muscle itself. Occasionally a heart attack victim experiences additional heart attacks within 24 to 72 hours after the initial attack. Consequently, it may become necessary to quickly remove the chest cable leads of the EKG when a patient is experiencing another heart attack in order to administer CPR, massage the heart or administer drugs. Accordingly, valuable seconds are often lost in removing the chest cable leads of the EKG device in order to administer aid to the patient.

Another problem in conjunction with the above problem is the desirability of removing only the cable leads necessary to administer aid, so that the remaining leads can continuously monitor the electrical activity of the heart during the heart attack. This informs the physician or nurse as to the effectiveness of the aid given to the heart attack patient, in addition to determining the extent of the damage to the heart.

Another problem associated with attaching the leads of an EKG device to a patient is that the leads are attached to a patient merely by a viscous gel composition. The viscous gel composition is necessary to transmit electrical activity from the patient to the EKG device. However, the gel is often insufficient by itself in retaining the leads in position on the patient. Generally, the weight of the lead cable is sufficient to detach it from the patient. Consequently, not only is entanglement a problem, as discussed above, but retention of the leads on the patient is a frequent problem.

The following patents disclose various methods of overcoming the entanglement problem and the problems of removal of the chest leads of the EKG device.

U.S. Pat. No. 3,991,747 to Stanly et al discloses a plurality of electrodes affixed to the upper torso of a patient in which the cable leads extend from a small radio transmitter also positioned upon the upper torso of the patient which sends the detected electrical activity of the heart in the form of radio signals to an EKG device. By employing very short cable leads and a radio transmitter, no cables droop from the EKG device to the patient so as to avoid the possibility of entangling the technician or nurse. This device which depends upon battery power, may yield erroneous signals as the batteries weaken in power. Additionally, the radio transmitter may be susceptible to other electronic interference particularly from hospital electronic equipment which may cause erroneous readings.

Another problem with the above device is that only chest electrode leads are employed for an EKG. If a patient suffers a heart attack and it is necessary to remove the electrode leads to administer aid to the patient, the entire device must be removed especially because the radio transmitter is normally positioned adjacent the heart of the patient. Thus, no electrodes remain attached which are capable of monitoring the heart attack and the progress of the aid given.

U.S. Pat. No. 4,328,814 to Arkans teaches a plurality of electrodes attached to a single junction connector which mates with a corresponding connector having one cable leading to the EKG device. This device is designed for an adult patient so that patients having larger or smaller torsos will have difficulty in using the device because the electrodes cannot be easily adjusted to accommodate a smaller or a larger torso. Additionally, in the event of a heart attack, the plurality of electrodes must be disconnected from the EKG device by disconnecting the main connectors and then detaching the plurality of electrodes. No electrodes remain on the patient to monitor the heart attack.

Moreover, all the electrodes are held in position by the viscous gel composition placed between the electrode and the skin of the patient. A restless patient frequently detaches the electrodes by a simple movement, such as raising the arm.

U.S. Pat. No. 4,353,372 to Ayer discloses a plurality of electrodes which plug into a junction box connected to an EKG device. Each of the electrodes includes wires molded into a central cable system which joins the junction box. This device, like those discussed above, does not include means for quickly removing the chest electrodes in an emergency situation. Rather, the junction box must be disconnected first and then each of the electrodes must be detached. Although each electrode has a wire lead from the main molded cable, which may permit some adjustment in the placement of the electrodes on the upper portion of a human torso, the device is not entirely adequate for large adults or very small children because of the limited adjustment of each electrode. Additionally, this device, like the previously described device, holds the electrodes in position by the viscous gel composition, and the electrodes frequently become detached as explained above.

Because of the inadequacies of prior art devices, such as those discussed above, there is a need for a system which prevents EKG electrode leads from becoming entangled with one another; aids in preventing the electrodes from becoming detached by supporting the electrode leads in a manner other than solely by the viscous gel composition; provides a procedure to quickly remove the chest electrodes while leaving the remaining electrodes in position when it is desired to administer aid to a patient having a heart attack; and is adjustable, thus permitting its use on both large and small human torsos.

SUMMARY OF THE INVENTION

The present invention comprises a cable harness having a central unit which rests upon the torso of the patient. The central unit has two sidewardly extending abdominal arms which are spring loaded to clamp the torso thus holding the overall device in position. Extending from the outer end of each abdominal arm is a side arm which projects to the axilla of the patient. From each abdominal arm and side arm extends an electrode having telescoping leads so as to be adjustable for all sizes of human beings.

The top of the central unit includes a swivel connection to which is attached a boom capable of swiveling in a 360° fashion, if desired. The boom has attached thereto a plurality of chest electrodes with their associated wiring incorporated into the boom. Each electrode has a stainless steel base with curved edges to prevent injury to the patient while positioning and removing the electrodes.

The device of the present invention can be positioned on a patient and adjusted for the patient's size by telescoping the electrodes from the device such that they fit the body size of the patient.

Once the cable harness of the present invention has been placed in position and the electrodes have been attached to the properly designated locations on the upper and mid torso, the electrodes attached to the chest of the patient may be quickly removed in an emergency by lifting upwardly on the boom and rotating it out of the way. This permits a physician for example, to administer medical aid such as CPR, heart massage or drugs, while the remaining electrodes remain in position to monitor the heart. If it is desirable to completely remove the entire cable system of the present invention from the patient, then the operator may grasp the central unit and pull the entire device away from the torso of the patient by pulling the central unit upwardly and toward the feet of the patient.

In the broadest sense, the present invention comprises a cable harness including one o more laterally projecting arms extending from a central unit and a boom having one or more electrodes interconnected therewith wherein said boom is pivotally mounted atop the central unit so that it may rotate laterally to a position which would not interfere with the administration of medical aid. Optionally, the laterally projecting arms of the central unit may contain additional electrodes which are connected to the lateral arms by telescoping members. Note that the removal of the boom and its corresponding electrodes permits heart message or CPR to be conducted while maintaining the limb lead electrodes associated with the laterally projecting arms of the cable harness in position.

DESCRIPTION OF THE PREFERRED EMBODIMENT

Figure 1:
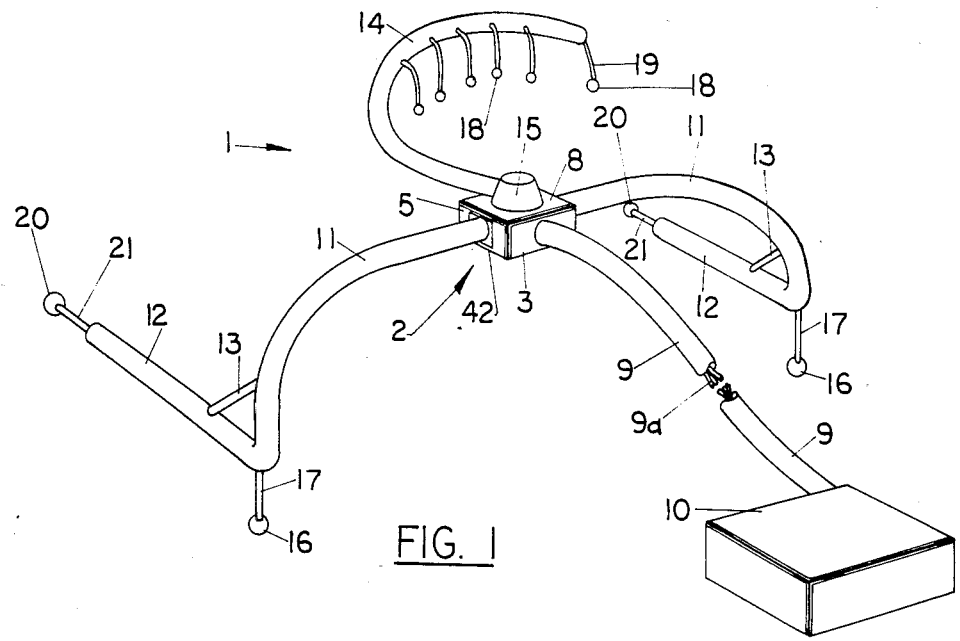
FIG. 1 is a fragmentary perspective view of the wiring harness of the present invention.

The overall cable harness device 1, as illustrated in FIG. 1, comprises a central unit 2 in the form of a housing having a rear side wall 3, a right side wall 4 (see FIG. 6); a left side wall 5, a front side wall 6 (see FIG. 6); a bottom wall 7 (see FIG. 6); and a top wall 8, which together form an enclosed housing. Extending through the rear side wall 3 is a cable 9 which extends trom the central unit to the EKG machine or device 10. Generally the EKG device 10 is located remote from the central unit and patient and is generally placed upon a movable cart for ease in portability and visibility. Inside cable 9 are ten wires extending to ten electrodes, as will be explained later.

Figure 2:
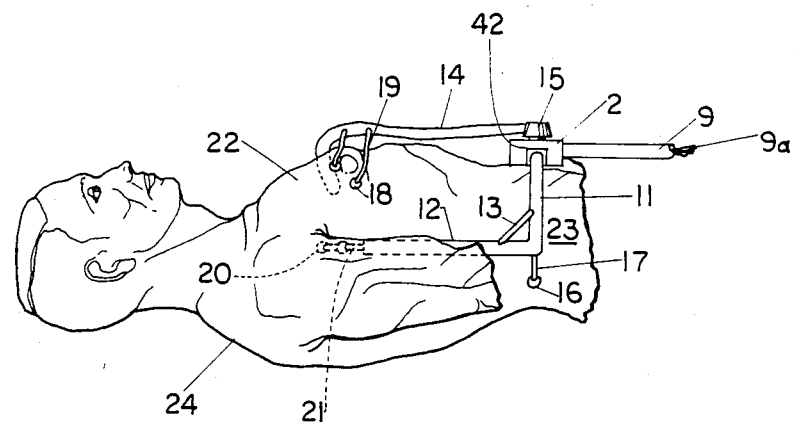
FIG. 2 is a fragmentary side elevation view of the wiring harness of the present invention as it is properly positioned upon the upper and middle torso of a patient.

Extending from the right side wall 4 and the left side wall 5 are a pair of curved lateral arms 11 designed to grip the torso of the patient as shown in FIG. 2. A side arm 12 extends from the terminal end of each lateral arm 11. The side arm 12 is substantially perpendicular to the lateral arm 11 at the juncture of the arms. In order to strengthen the juncture of the lateral arm 11 and the side arm 12, a side brace 13 extends between the lateral arm and the side arm.

A boom 14 is attached to a swivel 15 which is mounted upon the top wall 8 of the central unit 2. The swivel 15 is designed to rotate in a 360° fashion such that the boom can be positioned in an operating position, or it can be rotated to a position which will not interfere with the physician, nurse or medical technician.

At the terminal end of each lateral arm 11, near the juncture of the side arm 12, a lateral arm telescoping extension 17 is coupled to a lateral arm electrode 16. At the terminal end of the side arm 12 is a side arm telescoping extension 21 which terminates in a side arm electrode 20. The boom 14 has at least one, and preferably six lead wires, one of which is shown at 19, which terminate in chest electrodes 18, one electrode for each lead wire.

Generally the entire cable harness 1 can be made of metal or plastic or a combination of both. If the electrodes are a composite plastic/metal material, the material should be capable of conducting electrical current. Preferably, the electrodes 16, 18 and 20 are made of metal. More preferably, the electrodes are made of stainless steel or other metals which are non-oxidizing or substantially non-oxidizing, such as copper or bronze. Additionally, the electrodes must be relatively chemically inert with respect to both the conducting gel and the salts and oils produced by the body and secreted through the pores of the skin. It is preferable that the lead wires also be made of metal because metal has the least resistance to electrical current than most other materials.

FIG. 2 illustrates the position of the cable harness device as it is properly positioned upon a patient. The central unit 2 is generally placed upon the stomach or lower abdomen 23 of the patient and the boom 14 extends the chest electrodes 18 upwardly to the area surrounding the heart (e.g area 22). The side arms 12 position electrodes 20 on the sides of the patient adjacent the axilla, while the lateral arms 11 position electrodes 16 near the last bottom side rib or innominate bone of the pelvis. The contour of the lateral arms 11 is configured to conform substantially to the shape of a human torso.

Figures 3, 4:
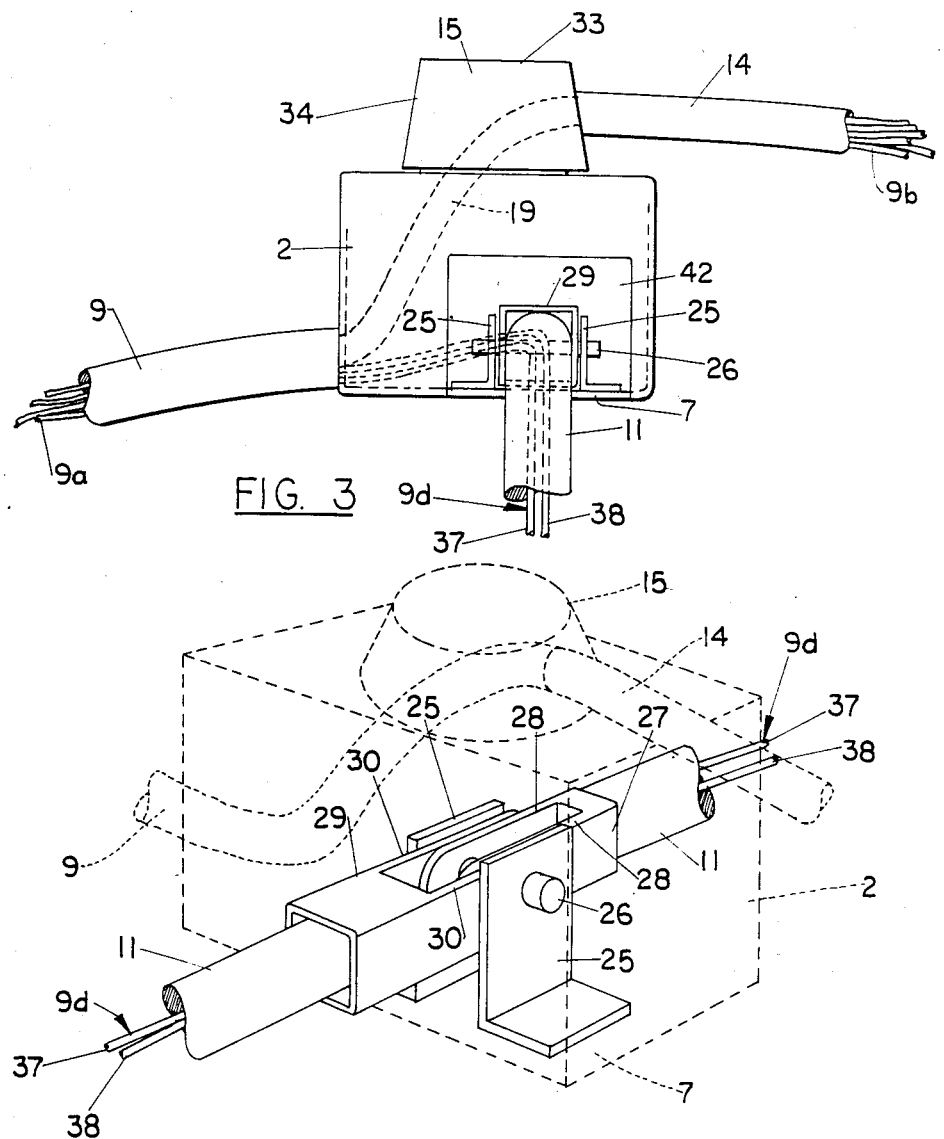
FIG. 3 is an enlarged fragmentary side elevation view of the central unit of the present invention.
FIG. 4 is an enlarged fragmentary side perspective view of the lateral arm attachment arrangement with the central unit box shown in phantom.

FIG. 3 illustrates an enlarged lateral view of the central unit 2. As previously discussed, main cable 9 is a composite of ten lead wires shown at 9a, six of which are shown at 9b and continue through swivel 15 and boom 14 to the six chest electrodes 18, while four of the wires branch into respective wire pairs 9d associated with each lateral arm 11. One wire 38 associated with wire pair 9d is connected to side arm electrode 20 (see FIG. 8) while the other wire 37 of wire pair 9d is connected to the lateral arm electrode 16 (see FIG. 7). Each side wall 4 and 5 of housing 2 contains an aperture 42 through which extends the associated lateral arm 11.

Figure 5:
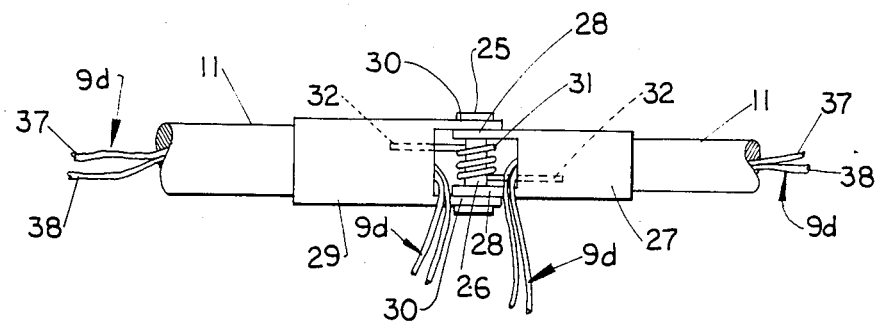
FIG. 5 is an enlarged fragmentary bottom view of the lateral arm connection.

The innermost ends of lateral arms 11, as illustrated in FIGS. 4 and 5, are telescopically received within and attached to square conduits 27 and 29, respectively. The lateral arms may be secured to conduits 27 and 29 by any conventional means such as, for example, with adhesive. Square conduit 27, which is slightly smaller than conduit 29, terminates in a rearwardly extending yoke comprising a pair of spaced parallel arms 28, while conduit 29 terminates in a forwadly extending yoke comprising a pair of spaced parallel arms 30 such that arms 28 are fitted between arms 30. A pair of L-shaped upwardly standing leg stands 25 are securely fastened to bottom wall 7 of central unit 2, and are spaced outwardly of arms 30. Arms 30 as well as arms 28 are pivotally attached to leg stands 25 by means of a pivot pin 26 which passes through cooperating coaxial apertures in leg stands 26, arms 28 and arms 30, respectively. It will be observed that this arrangement provides independent pivotal support for lateral arms 11.

Around the pivot pin 26 is provided a coil spring 31 having elongated oppositely directed ends 32 which extend into square conduits 27 and 29, respectively. The coil spring 31 biases conduits 27 and 29 downwardly toward the bottom wall 7 of the central unit 2, thereby biasing the lateral arms 11 toward one another to better grip the sides of the upper turso of the patient between lateral arms 11.

Figure 6:
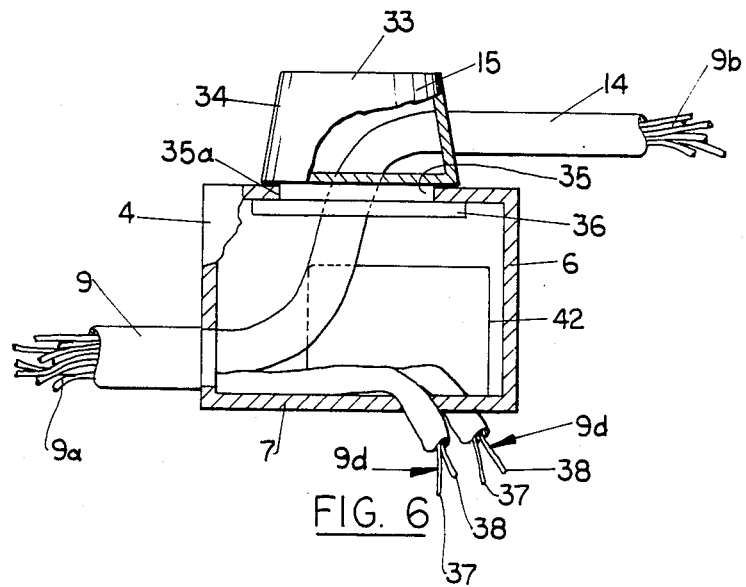
FIG. 6 is an enlarged fragmentary partially cross sectional view of the boom swivel as it attaches to the top surface of the central unit of the present invention.

The swivel 15, illustrated in FIGS. 3 and 6, comprises a hollow frustroconical portion 34 with a truncated top wall 33. The rigid boom 14 is connected to and extends outwardly from the frustoconical portion 34 of the swivel 15. The lower portion of swivel 15 terminates in a hollow cylindrical portion 35 which extends through a circular opening 35a in upper wall 8 of central unit 2 so that swivel 16 is free to rotate. The lower part of cylindrical portion 35a terminates in an annular flange 36 having a diameter greater than the diameter of opening 35a. This construction prevents swivel 15 from becoming detached from the center unit 2, particularly where the boom 14 is pulled upwardly as to remove the electrodes and boom from the area surrounding the heart in the event a heart message or CPR is necessary.

Figure 7:
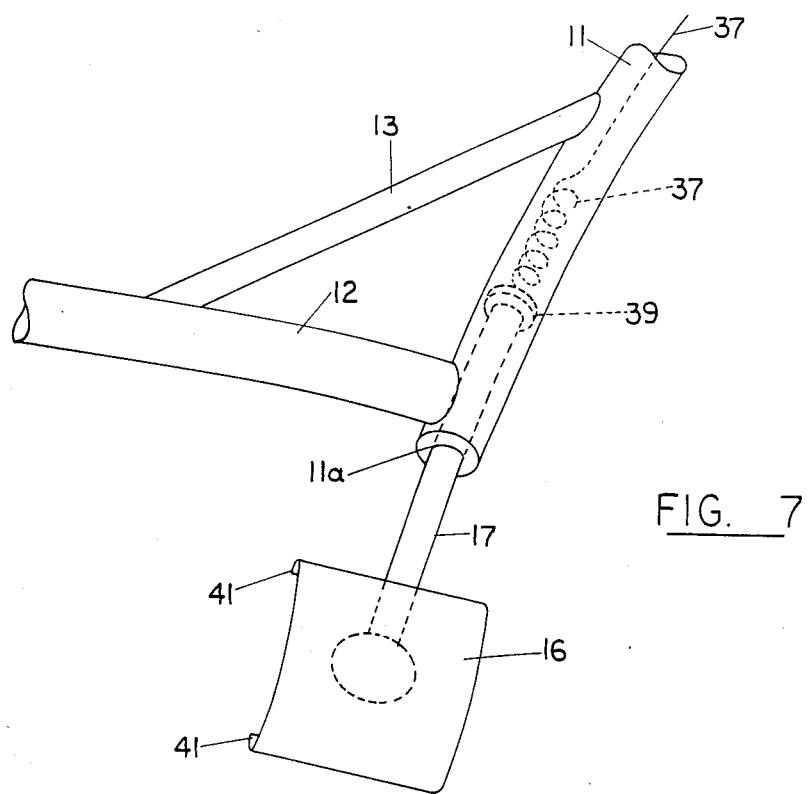
FIG. 7 is an enlarged fragmentary perspective view of an electrode telescopingly attached to one of the lateral extending arms.

Illustrated in FIG. 7 is the generally square plate-like electrically conducting lateral arm electrode 16 which has edges 41 which are curled away from the side of the electrode which contacts the patient. This construction permits the electrode to easily slide up and down with respect to a patient in a horizontal position so that the entire apparatus can be removed quickly from the patient in an emergency without cutting or scraping the patient.

Electrode 16 is attached to the lateral arm 11 by means of an electrically conducting lateral arm telescoping extension 17 which is telescopically received within hollow lateral arm 11 through an opening 11a in the end of the lateral arm. The innermost end of lateral arm telescoping extension 17 includes disc-like stop member 39, as shown in FIG. 7, which prevents the extension 17 from becoming disengaged from arm 11. The lateral arm electrode wire 37 is attached to stop monitor 39 and is coiled within lateral arm 11 as shown in FIG. 7 such that it may easily extend and retract with the electrode without becoming detached therefrom.

Figure 8:
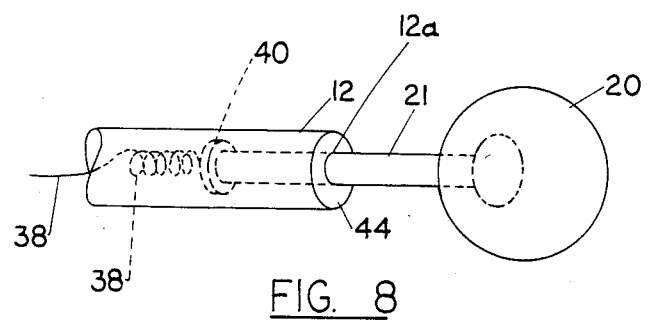
FIG. 8 is an enlarged fragmentary side elevation view of an electrode telescopingly extended from the side arm.

The side arm electrode 20, which in operation is placed adjacent to the axila of the patient, is illustrated in FIG. 8. The electrically conducting disc-like electrode 20 is generally circular in shape, although any shape may be employed. Electrode 20 is attached to the electrically conducting side arm telescoping extension 21. Extension 21 is telescopically received within hollow side arm 12 through an opening 12a in the terminal end of the side arm. The innermost end of extension 21 is provided with an electrically conducting disc-like stop member 40 which prevents extension 21 from becoming disengaged from arm 12. Side arm electrode wire 38 is coiled to permit the electrode 20 to be retracted and extended without the lead wire becoming detached.

It will be understood that a relatively tight fit may be provided between the outer peripheries of the stop members and the inner wall of their associated arms, or between the outer surface of the extensions 17 and 21 and the associated opening through which they are received, or both, to permit the electrodes to be retained in a desired extended or retracted position. Alternatively, spring means may be provided to bias extensions 17 and 21 to a desired position. In addition, although lateral arm electrode 16, illustrated in FIG. 7, is shown as being substantially square with curved edges 41, it can be any shape, such as a flat disk shape, like side arm electrode 20, or semispherical in shape, or the like, so long as the electrode has the ability to adequately contact the patient through the gelling composition in order to receive the electric signals, and to be quickly removed from the patient in an emergency, without scratching or cutting the patient. These comments apply equally to all of the electrodes.

In operation, the cable harness device 1 of the present invention is first brought into position over the torso of the patient so that central unit 2 rests on the patient's abdomen or lower chest as illustrated in FIG. 2. Lateral arms 11 are then pivoted downwardly and inwardly so that electrodes 16 press against the sides of the patient near the last bottom side rib or innominate bone of the pelvis. If necessary, electrodes 16 may be extended or retracted as previously described in order to make firm electrical contact with the outer surface of the patient's skin.

In a similar manner, electrodes 20 may be moved inwardly or outwardly to make good electrical contact with the sides of the patient adjacent the axilla.

Finally, boom 14 may be swiveled to a position overlying the chest of the patient as illustrated in FIG. 2 so that electrodes 18 are in the appropriate position for attachment to the area surrounding the heart, for example area 22 as illustrated in FIG. 2.

In removing the harness device of the present invention from the patient, it will be observed that the entire assembly may be lifted upwardly as a single unit in the event of an emergency. Alternately, one or both lateral arms 11 may be pivoted upwardly to disengage them from the patient's body. Furthermore, boom 14 may be easily pivoted out of the way of the patient's chest.

As described previously, the device of the present invention has the characteristics of being able to adapt to practically any size human being because the lateral arms are spring loaded and thus hug the sides of the patient, and because the electrodes are the telescoping type thus permitting their adjustment for any size patient. Additionally, the present invention permits the chest electrodes to be quickly removed from the chest of the patient in the event of a cardiac arrest which would require heart message or CPR, while permitting the side arm electrodes and the lateral arm electrodes to continuously monitor the heart. Furthermore, if it is desirable or necessary in emergency situations to remove the entire cable harness device, it can be grasped at the central unit 2 and pulled upwardly and outwardly away from the patient, thus quickly removing the entire apparatus from the patient so that further medical treatment can be given to the patient.

It will be understood that various changes in the details, steps, materials and arrangements of parts, may be made within the scope and principle of the present invention as expressed in the appended claims.

What is claimed is:

1. A cable harness device for use with an EKG machine or the like comprising:
   a central support unit;
   at least one pair of laterally extending elongated arms mounted to said central unit, each of said arms supporting an EKG electrode for engagement with a patient's upper torso;
   an elongated boom mounted to said central unit and supporting an EKG electrode for engagement with a patient's chest area; and
   means for electrically connecting said electrodes to an EKG machine.

2. The cable harness device of claim 1 wherein each lateral arm has attached thereto a side arm.

3. The cable harness device of claim 2 in which each of said side arms has at least one EKG electrode attached thereto positioned to contact a patient's axilla area.

4. The cable harness device of claim 2 wherein said side arm electrode is disk shaped.

5. The cable harness device of claim 2 including adjustment means for moving said side arm electrodes toward or away from said side arms.

6. The cable harness device of claim 5 wherein said adjustment means comprises means for telescopically connecting said lateral arm electrode to its associated lateral arm and for telescopically connecting said side arm electrode to its associated side arm.

7. The cable harness device of claim 1 including means for biasing said arms toward each other so that said electrodes are pressed into contact against a patient's upper torso.

8. The cable harness device of claim 2 wherein said side arm is perpendicular to said lateral arm at their juncture.

9. The cable harness device of claim 2 including adjustment means for moving said lateral arm electrodes toward and away from said lateral arm and for moving said side arm electrodes toward and away from said side arms.

10. The cable harness device of claim 1 including means for rotatably attaching said boom to said central unit.

11. The cable harness device of claim 10 wherein said attaching means allows said boom to rotate in a substantially horizontal plane.

12. The cable harness device of claim 1 wherein said boom is curved.

13. The cable harness device of claim 1 in which said at least one electrode on said boom is a plurality of electrodes spaced along said boom so as to contact spaced locations on a patient's chest.

14. The cable harness device of claim 3 wherein said plurality of electrodes comprises six electrodes.

15. The cable harness device of claim 1 wherein said at least one lateral arm electrode comprises a plate-like member having at least two opposed arcuate edges.

16. The cable harness device of claim 1 including adjustment means for moving said lateral arm electrodes toward or away from said lateral arms.

17. The cable harness device of claim 1 including means for pivotally attaching said lateral arms to said central unit such that said arms are vertically adjustable.

18. A cable harness device for use with an EKG machine or the like comprising:
   a central support unit;
   at least one pair of laterally extending elongated arms pivotally mounted to said support unit so as to be vertically adjustable, each of said arms supporting an EKG electrode for engagement with a patient's upper torso;
   an elongated boom pivotally mounted for rotation in a substantially horizontal plane to said central unit and supporting a plurality of EKG electrodes for engagement with a patient's chest area; and
   means for electrically connecting said electrodes to an EKG machine.

19. The cable harness device of claim 18 including means for biasing said lateral arms toward each other so that said lateral arm electrodes are pressed into contact against the patient's upper torso.

20. The cable harness of claim 19 wherein each of said lateral arms supports a second EKG electrode for engagement with a patient's axilla area.

21. The cable harness device of claim 20 including adjustment means for moving said lateral arm electrodes toward and away from said lateral arm.

* * * * *